(12) United States Patent
Kramer et al.

(10) Patent No.: US 8,474,225 B2
(45) Date of Patent: *Jul. 2, 2013

(54) DECAPPING SYSTEM

(75) Inventors: Reinhold Kramer, Peissenberg (DE);
Stephan Sattler, Starnberg (DE); Uwe Mertsch, Starnberg (DE)

(73) Assignee: Roche Diagnostics Operations, Inc., Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/471,786

(22) Filed: May 15, 2012

(65) Prior Publication Data

US 2012/0222389 A1    Sep. 6, 2012

Related U.S. Application Data

(63) Continuation of application No. 12/197,422, filed on Aug. 25, 2008, now Pat. No. 8,205,413.

(30) Foreign Application Priority Data

Aug. 29, 2007 (EP) .................................... 07115230

(51) Int. Cl.
*B67B 7/18* (2006.01)

(52) U.S. Cl.
USPC ................. 53/381.4; 53/367; 53/368

(58) Field of Classification Search
CPC ................. B67B 3/20; B67B 7/14; B67B 7/18
USPC ...... 53/317, 331.5, 367, 381.4, 368; 81/3.08, 81/3.09, 3.2, 3.32, 3.33, 3.39
IPC ........................................ B67B 3/20,7/14, 7/18
See application file for complete search history.

(56) References Cited

U.S. PATENT DOCUMENTS

| | | |
|---|---|---|
| 1,860,954 A | 5/1932 | Risser |
| 2,130,317 A | 9/1938 | Clarke |
| 3,683,598 A | 8/1972 | Van Zijp |
| 3,686,824 A | 8/1972 | Rink et al. |
| 3,775,829 A | 12/1973 | Rice |
| 3,803,795 A | 4/1974 | Ouellette |
| 3,830,390 A | 8/1974 | Gach |

(Continued)

FOREIGN PATENT DOCUMENTS

| | | |
|---|---|---|
| CA | 2 639 013 A1 | 2/2009 |
| EP | 0383564 A2 | 8/1990 |

(Continued)

OTHER PUBLICATIONS

U.S. Office Action dated Dec. 1, 2010, U.S. Appl. No. 12/197,422, filed Aug. 25, 2008.

(Continued)

*Primary Examiner* — Stephen F Gerrity
(74) *Attorney, Agent, or Firm* — Dinsmore & Shohl

(57) ABSTRACT

Decapping system for opening or closing reagent containers or cartridge systems closed by a lid which is removed and secured by a rotational movement and method thereof are disclosed. The decapping system has a centering unit at its lower end that provides a snap-in element which engages the lid, and a plurality of simultaneously driven and vertically movable screwing heads which compensates for variable heights and/or sizes of cartridge systems to be processed.

19 Claims, 10 Drawing Sheets

U.S. PATENT DOCUMENTS

| | | | |
|---|---|---|---|
| 3,987,535 | A | 10/1976 | Brown |
| 3,991,896 | A | 11/1976 | Miranda |
| 4,178,732 | A | 12/1979 | Pfleger |
| 4,265,071 | A | 5/1981 | Smith et al. |
| 4,295,320 | A | 10/1981 | Willingham |
| 4,535,585 | A | 8/1985 | Gardos |
| 4,979,350 | A | 12/1990 | Arnemann |
| 5,064,059 | A | 11/1991 | Ziegler et al. |
| 5,197,258 | A | 3/1993 | Johanek |
| 5,490,321 | A | 2/1996 | Kaneko |
| 5,533,407 | A | 7/1996 | Besnier |
| 5,819,508 | A | 10/1998 | Kraft et al. |
| 5,826,409 | A | 10/1998 | Slepicka et al. |
| 5,846,489 | A | 12/1998 | Bienhaus et al. |
| 5,862,934 | A | 1/1999 | Sattler et al. |
| 5,983,596 | A | 11/1999 | Corniani et al. |
| 6,202,278 | B1 | 3/2001 | Nakayama et al. |
| 6,216,340 | B1 | 4/2001 | Fassbind et al. |
| 6,255,101 | B1 | 7/2001 | Rousseau et al. |
| 6,398,281 | B1 | 6/2002 | Heimberg |
| 7,069,814 | B2 | 7/2006 | Chervak et al. |
| 7,181,892 | B1 | 2/2007 | Scott et al. |
| 7,846,395 | B2 | 12/2010 | Shaw |
| 8,205,413 | B2 * | 6/2012 | Kramer et al. ............... 53/331.5 |
| 2004/0241864 | A1 | 12/2004 | Sattler et al. |
| 2005/0013742 | A1 * | 1/2005 | Shaw .............................. 422/99 |
| 2005/0144908 | A1 | 7/2005 | Yang |
| 2006/0086065 | A1 | 4/2006 | Tomalesky et al. |
| 2008/0022808 | A1 | 1/2008 | Owen et al. |

FOREIGN PATENT DOCUMENTS

| | | |
|---|---|---|
| EP | 0504967 A1 | 9/1992 |
| EP | 0564970 A2 | 10/1993 |
| EP | 0869346 A2 | 10/1998 |
| EP | 1293783 A2 | 3/2003 |
| EP | 1452869 A2 | 9/2004 |
| EP | 2 031 407 B1 | 6/2012 |
| JP | 06-324051 | 11/1994 |
| JP | 11-230967 | 8/1999 |
| JP | 2003300591 A | 10/2003 |
| WO | 8301912 A1 | 6/1983 |

OTHER PUBLICATIONS

U.S. Office Action dated Nov. 19, 2010, U.S. Appl. No. 12/791,232, filed Jun. 1, 2010.

Final Rejection pertaining to U.S. Appl. No. 12/791,232 dated Apr. 22, 2011.

Restriction pertaining to U.S. Appl. No. 12/197,422 dated Apr. 20, 2010.

Office Action pertaining to U.S. Appl. No. 12/197,422 dated Jun. 7, 2010.

Notice of Allowance pertaining to U.S. Appl. No. 12/197,422 dated Apr. 13, 2012.

* cited by examiner

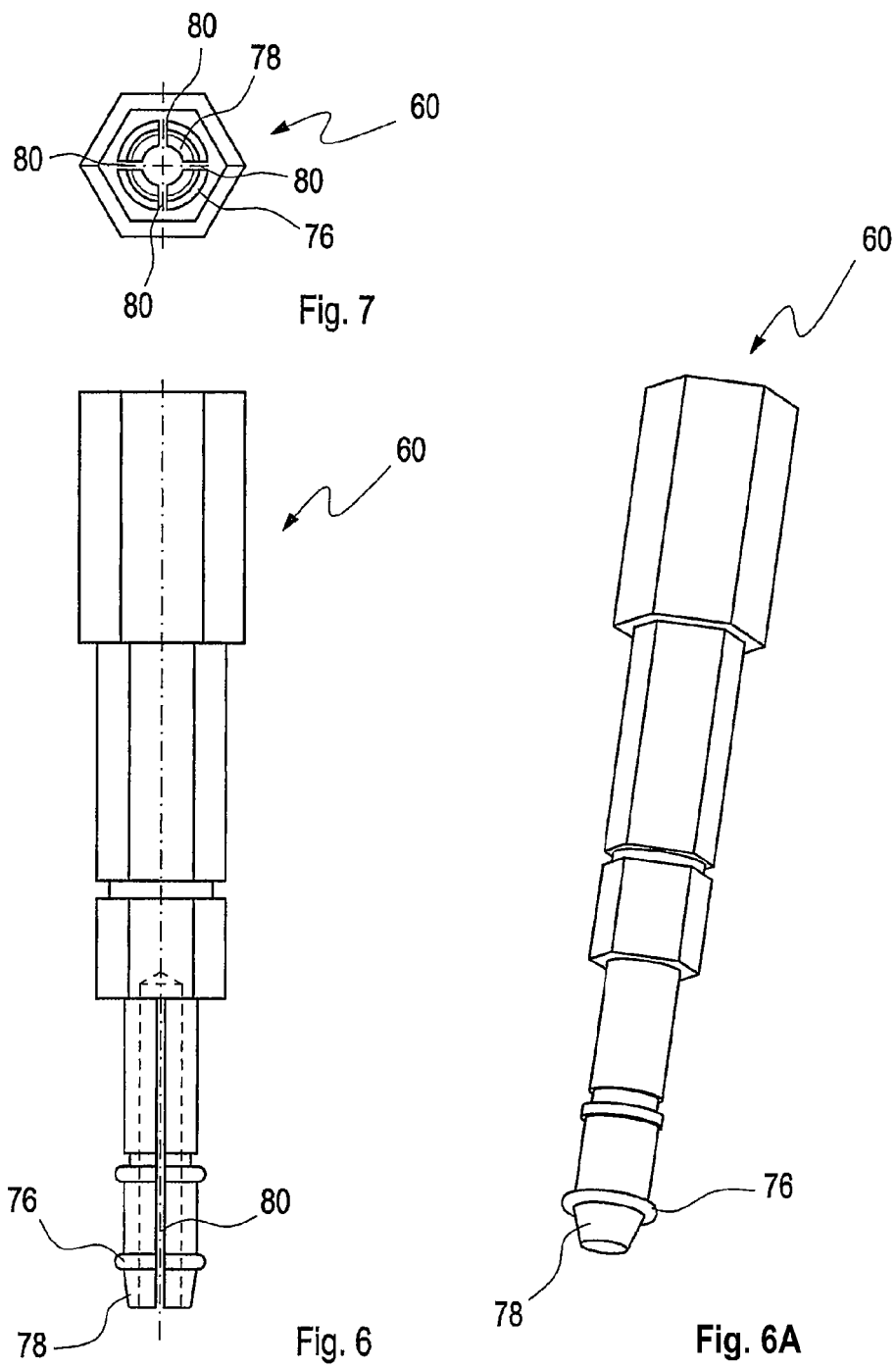

DECAPPING SYSTEM

CROSS-REFERENCE TO RELATED APPLICATIONS

This application is a continuation of U.S. patent application Ser. No. 12/197,422, filed Aug. 25, 2008, now U.S. Pat. No. 8,205,413, issued Jun. 26, 2012, which claims priority to European patent application EP 07115230.0, filed Aug. 29, 2007.

FIELD OF THE INVENTION

The present invention is related generally to automatic analysis devices, and in particular to a decapping system for automatic analysis devices in which a large number of reagents can be simultaneously accommodated and processed.

BACKGROUND OF THE INVENTION

It is desirable to permit, as far as possible, fully automatic handling of samples and reagents in analysis devices, so that no manual handling steps are necessary. This allows for simplification and acceleration of many analysis procedures and, still further, reduction of mistakes due to human error during the analysis procedure.

Stringent demands are placed on automatic analysis devices, especially in large-scale laboratories in which a high sampling rate must be permitted. Here, the analysis devices must be able to deliver the large number of reaction vessels with different samples and must be able to allocate these to different reagent containers. In this respect, pipetting devices, inter alia, are used to permit analysis of a sample, by addition of the corresponding reagents, and also further sampling processing steps. Thus, with fully automatic treatment of reagents and samples, even labor-intensive analysis procedures can be performed reliably and quickly, without requiring the involvement of specialized personnel for specialized analysis procedures. A demand placed on a fully or partially automated analysis procedure is, for example, the handling of sample quantities of different sizes, which require a corresponding quantity of reagents. A fully automatic analysis system has to satisfy a wide variety of requirements. There are analysis systems with a high throughput and others with a low throughput, as outlined in brief below.

In analysis systems for low throughput of reagents, the cycle time for liquid removal is approximately 4 to 10 seconds, with the pipetting needle piercing the vessel lid upon each removal. The reagent cartridge has a relatively long dwell time on the device, because of the low throughput. The dwell time is extended still further if the reagent cartridge contains seldom used reagents which are not often called upon and the reagent cartridge contains seldom used reagents which are not often called upon and which accordingly can remain for up to 4 weeks in the analysis system with low throughputs. In these reagent cartridges, there is a need for a high level of protection against evaporation.

In analysis systems distinguished by a high throughput of reagents, there is generally a short cycle time of between 1 and 4 seconds for the pipetting and the positioning of reagent rotor and pipetting needle. Because of the short cycle time, piercing of the funnels with the pipetting needle is not possible. Because of the high throughput of the reagents, the dwell time of the respective reagent cartridges on such analysis systems is only one to two days, for which reason an evaporation from an open flask can be tolerated here.

The handling of very small volumes is described for example in EP 0 564 970. The document discloses reagent containers which permit the removal of small volumes, and in which an evaporation or ageing of the remaining fluid in the container during further processing steps is avoided.

For this purpose, the reagent container has a suitably designed lid which, on the one hand, is suitable for removal of liquid, and, on the other hand, suppresses evaporation of the contents of the container. The lid has, in the middle of its base, a circular opening which is directed into the lid interior and opens out in a conical tip. For removing a sample, the tip of the cone is first pierced, so that a pipetting needle which is provided for removing very small sample quantities, can then be introduced into the vessel.

When the reagent has been removed from the vessel, a small opening remains exclusively at the tip of the cylinder. After removal of the sample, the small opening at the cylinder tip of the tip also ensures that almost no liquid evaporates from the reagent container and that the content of the vessel does not undergo changes due to the contact with, for example, atmospheric humidity or oxygen in the environment. Further details of this vessel closure can be taken from the prior art.

However, if a higher throughput and shorter processing time is necessary, the pipetting device, if it is to permit efficient handling of samples, may be equipped with correspondingly large pipetting tips to take up liquid. To ensure that in this case, too, the larger pipetting tips can still be inserted into the interior of the reagent vessel, a larger opening in the lid will be necessary.

As is described in U.S. Pat. No. 6,255,101 and U.S. Pat. No. 3,991,896, openings in a closure of a reagent vessel can be performed by means of a ball being pressed through the shaft of the reagent vessel lid with the aid of a pin. The ball is pushed into the interior of the reagent container, so that reagent liquid can then be removed through the shaft. Other possibilities, for example piercing a closure cap by means of a cannula as in document WO 83/01912, are conceivable as well. The diameter of the opening can be chosen according to the size of the shaft or the cannula.

In the prior art, this type of sample handling is used for example in analysis systems in the field of clinical-chemical analysis of biological samples. To remove a desired quantity of liquid reagent, the reagent is removed from the open reagent container and is transferred by means of an automatic pipetting device into a reaction cuvette. For each pipetting procedure, an electromechanically driven arm of the pipetting device is guided to an open reagent container, so that handling of samples can take place in the desired manner. The content of a standard reagent container in this case is sufficient for a large number of pipetting procedures. In this connection, it has been found that fluid evaporates during the analysis method before it can be completely used up, on the one hand through the removal of the reagent closure, and on the other hand through the creation of a large opening in a closure cap. Especially in rooms with low atmospheric humidity, considerable amounts of the reagent solution are often lost through evaporation. One consequence thereof is that the evaporation causes an increase in the concentration of the reagent in the fluid. By contrast, the volume of the reagent solution increases when using open reagent containers in rooms with relatively high atmospheric humidity, or through condensation water forming when cooled reagents are used, so that the reagent concentration decreases over the course of time. Moreover, when open reagent containers are used, there is an exchange of gas with the surrounding air, which among other things causes ageing of a reagent. Such effects on the reagent, in particular in the reagent concentration, result in a deterioration in the analysis precision. It has additionally been found that a removal of the reagent closure often has to be done manually. Under these circumstances, the laboratory personnel must take new reagent containers from their packaging and first of all remove the closure in order then to place the open reagent container in the analysis system in place of an empty reagent container. Since it often happens that many different reagents are needed at different times in one and the same analysis system, a manual handling by laboratory personnel requires considerable labor and time. When reclosing the containers, it must be additionally be ensured that the closures are not mixed up. In procedures carried out manually, the possible confusion of the closures represents a source of uncertainty.

In the prior art, therefore, methods are described which permit automatic removal of a reagent container closure. Document EP 0 930 504 discloses a lid-gripping device which is intended for automatic handling of a lid on sample vessels. The lid of the sample vessels in this case has a spike around which the lid-gripping device can grip. By means of a chuck, the lid is held so securely that, when the lid-gripping device is lifted, the lid is completely detached from the vessel, while a holding-down sleeve holds the vessel down to prevent lifting of the vessel.

The document U.S. Pat. No. 5,846,489 likewise discloses an automatic system for opening reagent vessels. According to this solution, a pin of a gripping device is inserted into a groove provided for this purpose in the lid. At one end, the pin has a bead which allows the pin to be clamped in the groove of the lid. The lid can then be removed from the reagent vessel by lifting the pin.

Moreover, U.S. Pat. No. 5,064,059 is related to a device which allows a lid to be removed from the reagent vessel. However, the prior art described herein discloses only an automatic opening of reagent vessels closed by a stopper. Usually, stoppers are only used to close test tubes in which, for example, blood or another liquid from the human or animal body is received, but not reagent vessels. A disadvantage of the prior art is in this case that the mechanisms described do not permit opening of a screw-type closure of a reagent vessel. In practice, however, it has been found that for reagent vessels which often contain a volatile fluid, a screwable closure is particularly suitable, since such a screw-type closure guarantees a reliable sealing of the vessel.

In the prior art, U.S. Pat. No. 6,216,340 describes the removal of a reagent closure which is secured on the vessel by screwing. In this case, opener and reagent lid interact in the manner of a bayonet closure. Through a guide groove formed in the reagent closure, the automatic opener can insert a pin along the guide groove by rotation into the lid, until this is mounted against a limit stop of the guide groove. If the rotational movement is continued in this direction, turning the lid off from the reagent vessel is possible. By rotating the opener in the opposite direction, the connection between lid and opener is released again. A disadvantage of the prior art is the fact that a precise production of the bayonet closure on the lid is an essential requirement for ensuring the functional reliability of the system. The screwing operation, after filling of the vessel, must guarantee a narrowly tolerated angle position of the bayonet closure and also have a good sealing effect.

Moreover, the opener must be guided with precision to the respective reagent vessel to permit engagement of the pin of the opener in the bayonet closure. This requires either a precise placement of the reagent vessels in the analysis system or a detection of position by the analysis system for the respective reagent vessel. Moreover, complex tools are needed for producing the reagent lid, with the result that the production costs are increased. Particularly in the case of reagent vessels handled as disposable articles, this is a considerable disadvantage. Before the opener, after removal of a first lid, can be used again to open reagent vessels, the lid additionally has to be removed from the opener. In the example described, additional measures are needed to do this, which measures permit rotation of the lid in the opposite direction, so that the lid can be removed from the opener.

EP 1 452 869 A2 is related to a system for automatic opening of reagent vessels. The reagent cartridge opening module for opening reagent vessels comprises a carrier which, at its lower end, has a catch element. The catch element locks securely a reagent vessel lid against rotation. Further, a centering unit is guided essentially inside the carrier. The centering unit has at its lower end a snap-in element which can engage in a snap-fit connection with a reagent vessel lid provided for this purpose, so that the reagent vessel lid clings to the snap-in element and at least partially follows the movement of the snap-in element.

EP 0 383 564 A2, is related to a stopper remover apparatus. A stopper remover is used for automatically removing a stopper in a container. The remover comprises container gripping means for gripping the container in stopper gripping means for gripping the stopper. The stopper gripping means is rotated about an axis by a motor while it grips the stopper. The remover features an annular ring having a plurality of spikes, terminating in points extending from its inner surface, the spikes being generally disposed on the ring so as to be non-radially aligned. The result is that the spikes positively grip the stopper only when rotated in the one direction, and slip off the stopper when rotated in an opposite direction.

U.S. Pat. No. 3,830,390 is related to a safety closure for medicine bottles or the like. That safety closure for a container has a threaded neck. The closure consists of a relatively stiff, inner-threaded cap and a relatively resilient outer driver. The inner cap has a circular top and a cylindrical skirt. There are a plurality of ribs on the outer side of the cap skirt at the periphery of the top. The driver has a cylindrical skirt and a top and is telescopically fitted over the cap. There is a series of inwardly and downwardly extending lugs at the inner side of the junction of the top and skirt of the driver. A spacer at the center top of the cap holds the driver in normal, vertically spaced position. The lugs have vertical front edges which extend downwardly a distance sufficient to extend between and engage the ribs for driving the cap onto the container neck. The lugs also have vertical back edges which do not extend downwardly such distance when the driver is in normal position. The cap is removed from the container by flexing the periphery of the driver downwardly to engage the back edges of the lugs with the grips on the cap. In another embodiment, the spacer is annular and holds the rim of the driver up, the lugs and ribs are at inner annular areas, the overcap and driver, respectively, and the central portion of the top of the overcap is flexed downwardly to engage the back edges of the lugs with the grips for unscrewing the cap.

U.S. Pat. No. 5,862,934 is related to a packaging system for liquid reagents. According to this packaging system for liquid reagents, two or more vessels with holding areas are combined by pressing a plug-on plate onto the holding areas of the vessels. For this purpose, the plug-on plate has two or more apertures, the cross-section of which essentially corresponds to the cross-section of the holding areas of the vessels. Plug-on plate and/or holding areas of the vessels can have stop elements, which, after the combination, hinder the separation vessels and plug-on plate.

The prior art solution according to EP 1 452 869 A2 is related to decapping of reagent containers with snap-on ball fixing. According to this system, a cartridge system includes at least one container having a threadedly fixed lid, to be opened and unthreaded and subsequently to be trashed. The system according to EP 1 452 869 A2 is limited insofar as, according to this solution, only one threaded lid is engaged by the system at a time. This limits the performance and does not allow for parallel processing. Further, only one height of a cartridge system and only one standardized height of containers to be opened is processed. This likewise limits the performance of the system according to EP 1 452 869 A2. A centering pin by means of which a lid is being seized after being unscrewed is essentially unprotected and therefore prone to damage. The screwing head requires for normal function exact positioning and does not compensate for more tolerances, such as tolerances which are inherent to manufacturing of the cartridge systems. Still further, the solution according to EP 1 452 869 A2 does not provide from active gripping positioning and holding of the cartridge during the unscrewing, i.e. the opening process of a single container provided with a threaded lid. Still further, for getting rid of the lid unscrewed and for performing a vertical movement of the screwing head, an additional horizontal movement or a rotational movement of the screwing head above a trash-opening is required.

SUMMARY OF THE INVENTION

In view of the above background, in one embodiment a decapping system for opening reagent containers or cartridge systems closed by a lid provided for this purpose, the lids being removed and secured by a rotational movement, is disclosed. The decapping system discloses a centering unit, the centering unit having at its lower end an element engaging a lid, wherein the decapping system has at least one driven and vertically movable screwing head compensating for variable heights and/or sizes of cartridge systems to be processed.

In another embodiment, a method for unscrewing lids from a cartridge system or from containers stored at randomized positions within the cartridge system is disclosed. The method discloses loading the cartridge system onto a surface arranged below a plurality of screwing heads, and providing the plurality of screwing heads adjacent an upper surface of the cartridge system. The method further discloses processing the cartridge system in one operating cycle which unscrews lids during an unscrewing operation, and moving lids unscrewed from the cartridge system or the containers stored within the cartridge system after processing thereof into a lid container, arranged underneath the surface on which the cartridge system is loaded.

These and other features and advantages of the invention will be more fully understood from the following description of some embodiments of the invention taken together with the accompanying drawings.

BRIEF DESCRIPTION OF THE DRAWINGS

The present invention is illustrated by way of example and not limitation in the accompanying figures, in which like references indicate similar elements, and in which:

FIG. 6 is a side view of a tensioning tool given in greater detail;

FIG. 6A is a perspective view of an alternative embodiment of the tensioning tool;

FIG. 7 is bottom view of a tip of the tensioning tool according to FIG. 6;

DETAILED DESCRIPTION

Figure 1B:
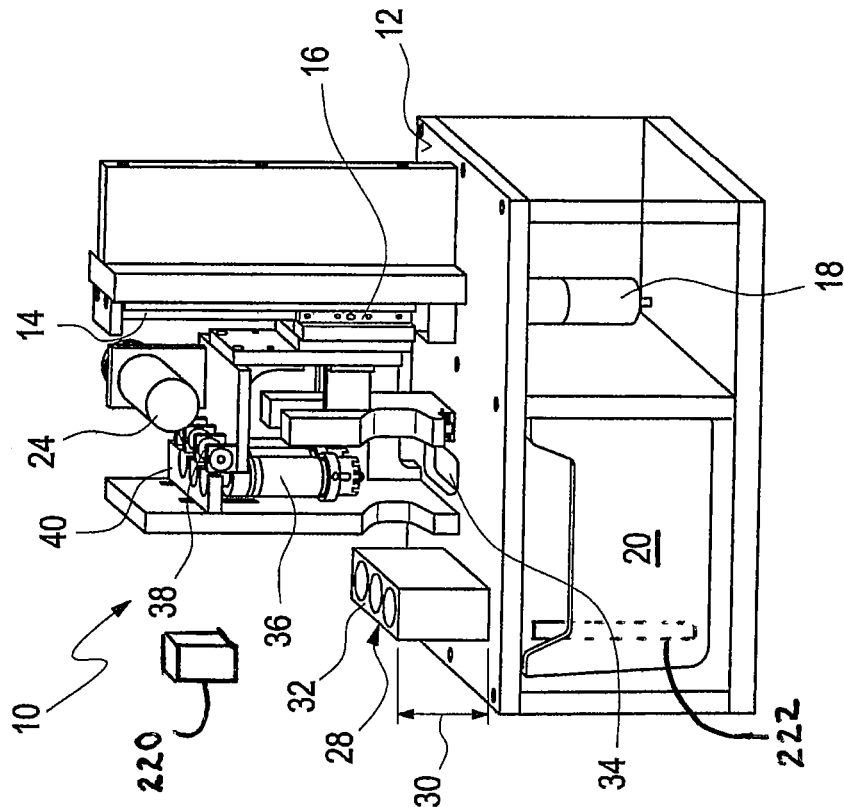
FIG. 1B is a second perspective view of the first embodiment of the present invention.
Figure 1A:
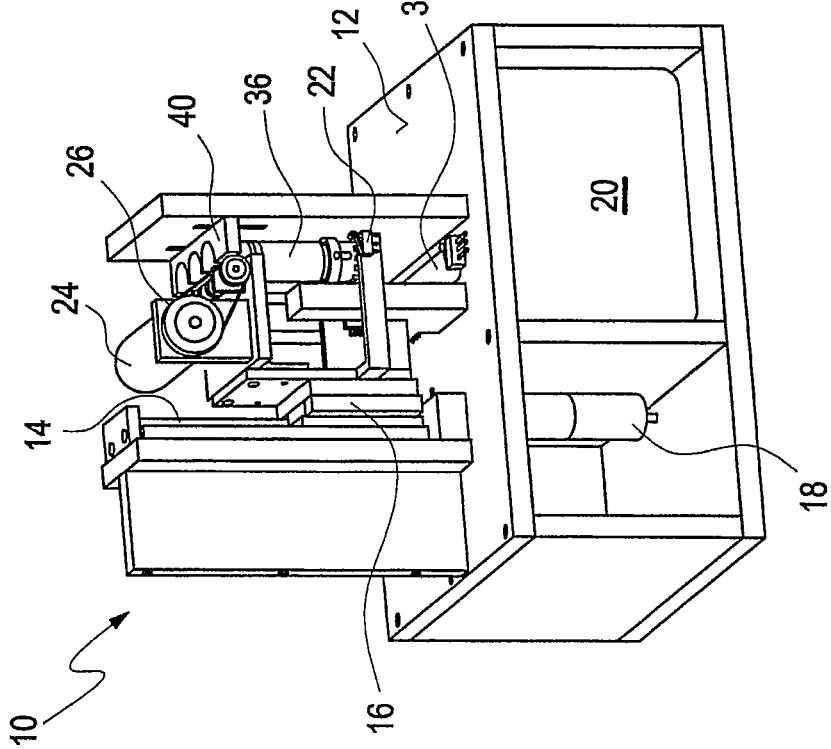
FIG. 1A is a first perspective view of a first embodiment of the present invention.

FIGS. 1A and 1B show different perspective views of the first embodiment of the present invention. FIG. 1A shows a decapping system 10 comprising a table, the surface of which is labeled with reference numeral 12. In vertical direction, a linear guide 14 is mounted on the surface 12 of the decapping system 10. By means of a linear drive 16, movable vertically along the linear guide 14, a plurality of screwing heads 36 is moved in vertical direction. From the linear drive 16, a screwing head drive 24 is mounted, driving a screwing head gear 26.

The screwing head gear 26 preferably comprises a worm/gear arrangement with which the plurality of screwing heads 36 is driven rotationally. With respect to the linear drive 16, the plurality of screwing heads 36 is mounted in substantially vertical direction, i.e. parallel to the direction of vertical movement of the linear drive, i.e. the Z-direction. The vertical movement of the linear drive 16, to which the plurality of screwing heads 36 is attached, is performed by a drive 18 mounted below the surface 12 to the linear guide 14. As is shown in FIG. 1A, the surface 12 of the decapping system 10 includes an opening 34. The opening 34 allows access to a lid container 20 mounted underneath the surface 12. Into the lid container 20, threaded lids 82 unscrewed by the plurality of screwing heads 36 from a number of reagent containing containers, arranged within a cartridge system 28, are being removed automatically upon unscrewing.

As is only schematically shown in FIG. 1A, a micro-switch 22 is arranged which limits the vertical movement of the linear drive 16, to which the plurality of screwing heads 36 is arranged in vertical direction, i.e. Z-direction.

FIG. 1B shows a different perspective of the first embodiment of the screwing/decapping system according to the present invention, as shown in FIG. 1A. FIG. 1B shows a cartridge system 28 having a height 30 being arranged on the surface 12 of the decapping system 10. Although preferably used for unscrewing reagent or liquid containers automatically, the decapping system 10 optionally may be used for screwing threaded lids onto the containers to perform a sealing function. An upper cartridge surface 32 extends according to the height 30 of the cartridge system 28 in vertical direction. As already being shown in FIG. 1A, the linear guide 14 having a drive 18 is arranged on the surface 12 of the decapping system 10.

FIG. 1B shows a stripping device 40, such as a stripping fork, arranged opposite the linear drive 16 which moves the plurality of screwing heads 36 in vertical direction, i.e. upwards or downwards. The stripping device 40 in the first embodiment of the present invention according to FIG. 1A is arranged stationary, the plurality of screwing heads 36 being movable relatively to the stripping device 40. By means of the stripping device 40, lids 82 unscrewed from containers contained within the cartridge system 28 are attracted by gravity and removed from the tips of the plurality of screwing heads 36 and are trashed through the opening 34 into the lid container 20 arranged underneath the surface 12 of the decapping system 10.

The screwing head gear 26 shown in FIG. 1A comprises an arrangement of a worm gear 38 and associated gears 48 to transmit a rotational movement to the plurality of screwing heads 36 assigned to the linear drive 16. Still further, FIG. 1A shows the screwing head drive 24 which is assigned to an essentially horizontally extending worm gear 38, meshing with a correspondingly shaped gear 48 of each of the screwing heads 36 of the plurality of screwing heads 36 shown in FIGS. 1A and 1B of the first embodiment of the present invention.

As can be derived from the first embodiment given in FIGS. 1A and 1B, respectively, by means of the screwing heads 36, a randomized number of containers arranged within a cartridge system 28 are processed at a time. The containers are arranged within the cartridge system 28 at randomized chosen positions. The device according to the present invention processes an entire cartridge system 28 which contains a number of containers in a synchronous manner. The decapping system 10 given in its first embodiment in FIGS. 1A and 1B processes the cartridge system 28 in one single cycle within which all threaded lids 82 are removed from the containers being arranged within the cartridge system 28. With the system according to the present invention, it is of no importance whether the cartridge system 28 contains one container filled with a reagent only or contains a number of containers. Still further, it is of no further significance, at which positions the containers filled with reagents are arranged within the cartridge system 28. The system according to the present invention detects automatically the respective height 30 of the cartridge system 28 in which the upper cartridge surface 32 extends. Thus, cartridge systems 28 provided with containers with liquid of different heights are processed.

Figure 2:
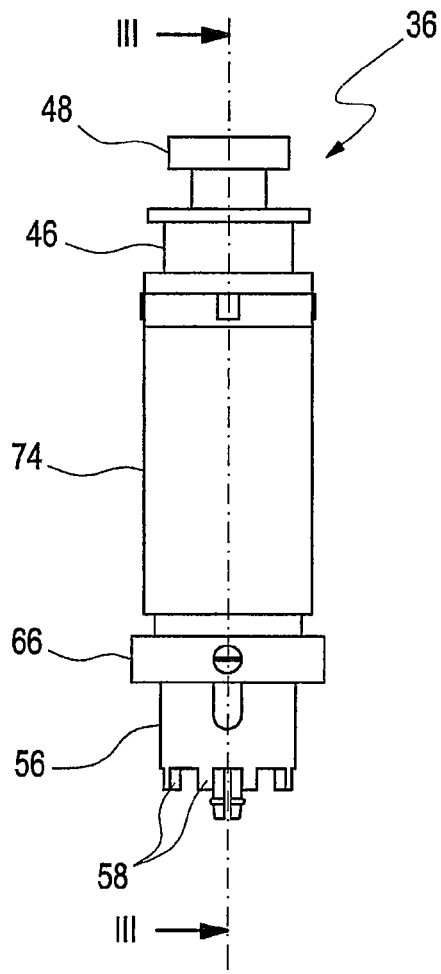
FIG. 2 is a side view of a single screwing head.
Figure 8A:
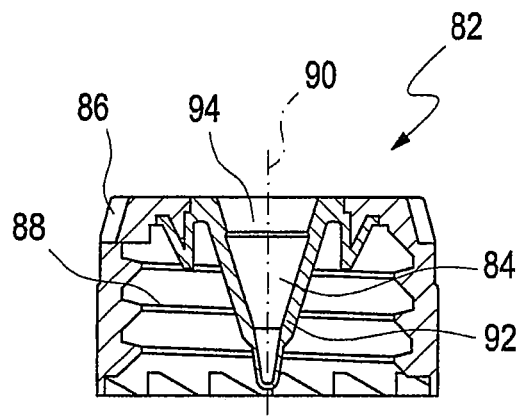
FIGS. 8A, and 8B are a cross section view and a side view, respectively, of threaded lids.
Figure 8B:
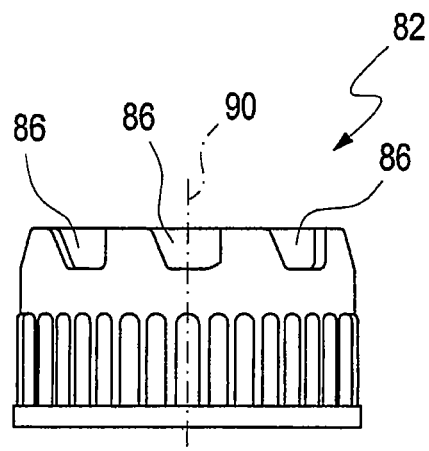

FIG. 2 shows a view of a single screwing head. According to FIG. 2, the screwing head 36 comprises a screw-support 42, which is, for instance, shaped as a jacket. The screwing head 36 comprises at its upper end the associated gear 48 which engages the worm gear 38 of the screwing head gear 26. Reference numeral 46 depicts a bearing with which the screwing head 36 is mounted within the linear drive 16, as shown in FIGS. 1A and 1B, respectively. On an outer circumference 74 of the screwing head 36, an annular-shaped removing device 66, particularly a ring member, is arranged. Below this removing device 66, a screwing ring 56 is arranged, having along its circumference a number of tooth-shaped protrusions 58 for engagement of grooves 86 arranged on the outer circumference of the threaded lid 82, as best shown in FIG. 8B. In the center of the screwing ring 56, a snap-in element or centering cone 78 is shown.

Figure 3:
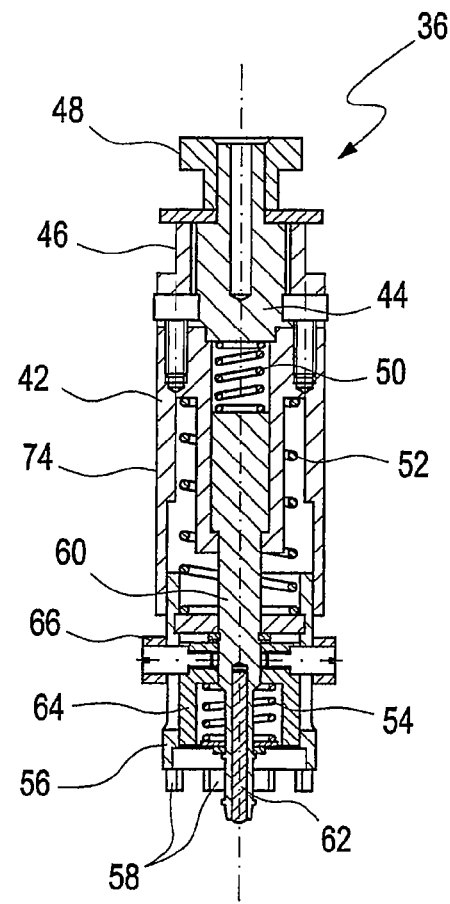
FIG. 3 is a cross section view taken along section line III-III through the screwing head of FIG. 2.

FIG. 3 shows a cross section through the screwing head given in FIG. 2. According to FIG. 3, the screwing head 36 comprises within the symmetrically jacket-shaped screw-support 42 an axis 44 surrounded by the bearing 46. Below the axis 44, a tensioning tool 60 is arranged. The tensioning tool 60 is shaped symmetrically and is given in greater detail in FIGS. 6 and 6A, respectively, which will be described below. On the axis 44, the worm gear 48 is mounted by means of which a rotational movement is transmitted to the screwing head 36 given in cross section in FIG. 3. Between the axis 44 onto which the worm gear 48 is mounted, and an upper surface of the tensioning tool 60, a first tensioning spring 50 is arranged. The tensioning spring 50 can be shaped alternatively according to the knowledge of the person skilled in the art. The tensioning tool 60 being biased by the first tensioning spring 50 is surrounded by a second tensioning spring 52 which in the embodiment according to FIG. 3 of the screwing head 36 has a helical-shaped design. The first tensioning spring 50 pretensions the crown-shaped screwing ring 56, which engages upon a downward directed movement of the screwing head 36 a rim of the lid 82. The protrusions 58 provided on the crown-shaped screwing ring 56 engage grooves 86 of the lid 82. The crown-shaped screwing ring 56 is movable with respect to the screw support labeled with reference numeral 42.

According to the cross section of the screwing head 36 given in greater detail in FIG. 3, the removing device 66 in ring shape is fixed and made stationary by bolt-shaped elements within the screwing head 36. The bolt allows for a vertical movement of the crown-shaped screwing ring 56 below the removing device 66. An opening 218 is arranged in the surface of the crown-shaped screwing ring 56, see FIG. 2, which allows for a movement of the crown-shaped screwing ring 56 relative to the element or bolt 216 fixing the removing device 66. FIG. 3 further shows a third tensioning spring 54 by means of which the screwing ring 56 is biased against a remover-tube 64. On the outer circumference at the lower end of the crown-shaped screwing ring 56, the tooth-shaped protrusions 58 engaging grooves 86 of the lid 82 as shown in FIGS. 8A, 8B, respectively, are shown. As shown in FIG. 3, the tensioning tool 60 comprises a centering pin 62, the centering cone 78 of which centers the lid 82 to be engaged by the tensioning tool 60 with respect to the protrusions 58 of the screwing ring 56 and the grooves 86 in the circumference of the lid 82, given in FIGS. 8A and 8B, respectively. Accordingly, the tensioning tool 60, with the centering pin 62 and centering cone 78, along with the linear drive 16 in one embodiment is considered a centering unit.

The third tensioning spring 54 allows for a vertical movement of the remover-tube 64 relative to the crown-shaped screwing ring 56. The second tensioning spring 52 allows for a relative movement between the crown-shaped screwing ring 56 to the screw-support 42. Finally, the tensioning tool 60 is being pretensioned by means of the first tensioning spring 50 arranged between the axis 44 and the upper planar surface of the tensioning tool 60.

Figure 4:
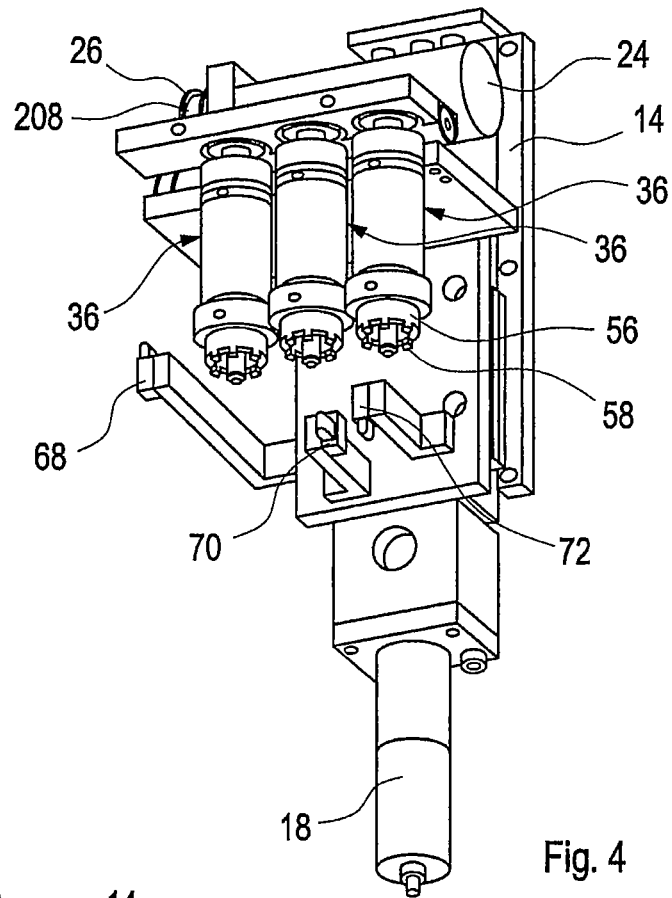
FIG. 4 is a perspective view of a screwing arrangement with a plurality of screwing heads.

FIG. 4 shows the decapping system having a plurality of screwing heads. According to the embodiment shown in FIG. 4, the linear guide 14 comprises at its lower end the drive 18 allowing for a vertical movement of the linear drive 16 in vertical direction. On the linear drive 16, the screwing head drive 24 is arranged, which, by means of the screwing head gear 26, simultaneously drives the screwing heads 36 arranged one by one. At the lower end of the screwing head 36, the crown-shaped screwing rings 56 are shown, given in greater detail in FIGS. 2 and 3, described above.

At the lower circumference of the crown-shaped screwing rings 56, the tooth-shaped protrusions 58 engaging the grooves 86 of the lids 82 are shown. In the perspective view of FIG. 4, the linear drive 16 comprises a first micro-switch 68 which is used as a Z-top_stop. By means of the first micro-switch 68, a throw-off of the lids 82, previously engaged is initiated. By means of a second micro-switch 70 Z-bottom_1, the presence of the upper cartridge surface 32 is detected and the rotational drive of the plurality of screwing heads 36 is activated. By means of the third micro-switch 72 according to the embodiment given in FIG. 4, the screwing, i.e. a rotational movement of the crown-shaped screwing rings 56 of the respective screwing heads 36 is initiated.

Figure 5:
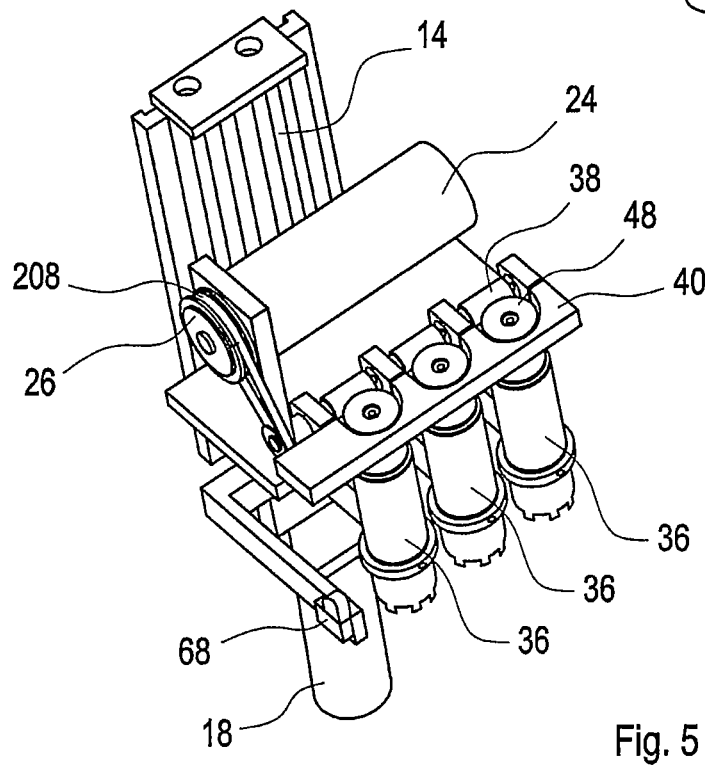
FIG. 5 is a perspective view of the plurality of screwing heads according to FIG. 4.

FIG. 5 shows a perspective view of the plurality of screwing heads according to FIG. 4, shown there from a lower perspective angle. According to FIG. 5, the linear guide 14 comprises a number of grooves, in which the linear drive 16 apt for movement in vertical direction (Z-direction) is guided. According to FIG. 5, the screwing head drive 24 engages by means of the screwing head gear 26, a worm gear 38 meshing with the respective worm gear 48—shown in FIGS. 2 and 3, respectively—of each of the screwing heads 36 according to FIGS. 2 and 3, respectively. By this drive 24, 38, 48, a rotational movement is transmitted to the crown-shaped screwing rings 56 arranged at the bottom end of the screwing heads 36. In the perspective view according to FIG. 5, the first micro-switch 68 (Z-top_stop), the contact of which initiates the removal of the lids 82 previously engaged by the crown-shaped screwing ring 56, is shown.

FIGS. 6, 6A and 7 show the tensioning tool 60 in greater detail which is arranged within the screwing head 36 shown in more detail in FIGS. 2 and 3, respectively. According to FIG. 6, the tensioning tool 60 comprises at its bottom end, above the centering cone 78, a holding protrusion 76, which in general is an annular extending ring. The tensioning tool 60 is provided with a plurality of longitudinally extending slits 80 which impose an elasticity to tongues of the tensioning tool 60.

FIG. 6A shows an alternative embodiment of the tensioning tool 60 given in FIG. 6. According to the embodiment given in greater detail in FIG. 6A, a holding protrusion 76 arranged above a centering cone 78 is given by an O-ring, made of a resilient rubber material, to present an example. By means of the O-ring, the lids 82, as best shown in FIGS. 8A and B, respectively, are engaged by the spring-biased tensioning tool 60. The cone area 78 is not slitted by longitudinal slits 80, since the elasticity for engaging the lids 82, as shown in FIGS. 8A and 8B, respectively, is provided by the resiliency or the elasticity of the rubber material of which the O-Ring is being made. Thus, according to the embodiment given in Figure A, a longitudinal slitting of the tensioning tool 60 is not necessary with this embodiment.

As is best shown in FIG. 7, the tensioning tool 60 is equipped with four longitudinally extending slits 80 resulting in four tongues being separated from one another. Upon a vertically downward movement of a screwing head 36 according to the present invention, the centering cone 78 provided with an annular extending holding protrusion 76, engages a funnel-shaped cavity 84 of a lid 82 as best shown in FIG. 8A.

The cross section of the tensioning tool 60 has the shape of a nut allowing an exact guidance of the tensioning tool 60 when pretensioned by tensioning springs 50, 52, as shown in FIG. 3, within the tensioning tool 60 used in the screwing head 36.

FIGS. 8A and 8B, respectively, show lids 82 screwed or unscrewed by the decapping system 10 according to the present invention. As is best shown in a cross section according to FIG. 8A, the lids 82 are symmetrically concerning an axis 90 and comprise an inner thread 88. The containers, filled to a certain extent with a reagent, have a threading surrounding their upper opening, the threading of the container matching the pitch of the inner thread 88 of the lid 82. Still further, the lid 82 comprises a funnel-shaped cavity 84 which is engaged by the centering cone 78 of the tensioning tool 60. The respective holding-protrusion of annular shape, see reference numeral 76, shown in the embodiments according to FIGS. 6 and 6A, respectively, engages the wall 92, limiting the funnel-shaped cavity 84 in the lid 82. Therefore, the centering cone 78 is moved into the funnel-shaped cavity 84 of the lid 82 until the annular holding protrusion 76 engages an inner protrusion 94 on the inner side of the wall 92 of the funnel-shaped cavity 84 of the lid 82. Due to the tensioning tool 60 and the crown-shaped screwing ring 56 of the screwing head 36 according to the present invention, being spring-loaded and being able to compensate a vertical movement, a vertical movement of the lid 82 engaged by the crown-shaped screwing ring 56 with respect to the container during rotational movement of the lid 82 relative to the container is compensated for. Thus, no adjusting of the screwing head 36 is necessary. Still further, the screwing head 36 can be fixed to the linear guide 14, the tensioning tool 60 and the crown-shaped screwing ring 56 each being able to compensate for a vertical movement of the lid 82. Due to the spring-loaded tensioning tool 60 and the spring-loaded crown-shaped screwing ring 56, a firm contact upon engagement of the protrusions 58 of the crown-shaped screwing ring 56 with the grooves 86 on the circumference of the outer wall of lids 82 is maintained.

FIG. 8B shows the lid 82 being shaped symmetrically with respect to its axis 90. Grooves 86 which are spaced apart from another along the circumference at the upper rim of the lid 82 are engaged by the tooth-shaped protrusions 58 arranged apart from another in an identical pitch of the crown-shaped screwing ring 56, as shown in FIGS. 2, 3, respectively.

The operation of the first embodiment of the present invention according to FIGS. 1A to 8B is realized as follows. Upon introduction of a cartridge system 28, comprising a number of containers with reagents sealed with the lids 82 according to FIGS. 8A and 8B, respectively, below the screwing heads 36, the presence of the cartridge system 28 is detected by at least one micro-switch 22, as schematically shown in FIG. 1A The micro-switch 22 is triggered upon contact with a respective side wall of the cartridge system 28, only. The presence of the cartridge system 28 initiates the lid-unscrewing cycle. The plurality of screwing heads 36 is moved by means of the linear drive 16 in downward direction. Upon contact of the second micro-switch 70 and the upper cartridge surface 32, the screwing head drive 24 is started, which imposes a rotation on each of the crown-shaped screwing rings 56 of each of the screwing heads 36. Detection of reaching the height 30 of the cartridge system 28 triggers the start of the screwing head drive 24. Therefore, the system according to the present invention is able to process cartridge systems 28 of variable heights 30.

The crown-shaped screwing rings 56 of the plurality of screwing heads 36 rotate and contact the upper surface 32 of the cartridge system 28, the tensioning tools 60 of the screwing heads 36 engaging by means of their centering cone 78 the lids 82 within the funnel-shaped cavity 84. Simultaneously, the protrusions 58 provided at the upper circumference of the crown-shaped screwing ring 56 engage the grooves 86 of the lid 82, as best shown in FIG. 8A. By means of the third micro-switch 72, the movement of linear drive 16 along the linear guide 14 in downward direction is stopped.

In this position, the lids 82 are being unscrewed from respective containers. The pitch of the inner thread 88 upon rotational movement of the lid 82 is compensated for due to the spring-loaded arrangement of the crown-shaped screwing ring 56, and the tensioning tool 60, respectively.

In case of a non-presence of a lid 82 in one of the three possible screwing positions, the crown-shaped screwing ring 56, particularly the centering cone 78 or a protection pin, contact the upper surface 32 of the cartridge system 28. Thus, the spring-biased screwing ring 56 compensates for the further vertical movement of the linear drive 16 at this position. In the case the crown-shaped screwing ring 56, particularly the centering cone 78 or the protection pin, engages a void space, i.e. a space of the cartridge system 28 where no container is stored, an intended or unintended vertical downward movement does not damage components (36, 56, 58), since no contact with other, fixed and stationary components is realized in this case.

Upon unscrewing of the lids 82, the lids 82 unscrewed are engaged by the crown-shaped screwing rings 56, particularly the protrusions 58 thereof engaging the grooves 86 of the lid 82. The linear drive 16 moves into vertical direction to move the unscrewed lids 82 into a distance above the cartridge system 28. The cartridge system 28 is now removed from the surface 12, the micro-switch, which detects the upper cartridge surface 32 of the cartridge system 28 according to the height 30 thereof and which initiates the screwing head drive 24, moves into its initial position, in which the screwing head drive 24 is switched off. Now, the cartridge system 28, the containers of which are being unscrewed, is removed. The complete removal of the cartridge system 28 out of the decapping system 10 according to the present invention is detected by a further micro-switch.

The linear drive 16 is moved by activation of drive 18 further into vertical direction. Upon contact of remover ring 66 with a stripping device 40, such as a stripping fork, the lids 82 previously unscrewed from the containers are stripped off from the centering cone 78, and the holding protrusion 76, respectively, of the tensioning tool 60. The lids 82 are removed by gravity through the opening 34 in the surface 12 of the decapping system 10 into the lid container 20 arranged underneath. The upper position of the linear drive 16 is likewise detected by a micro-switch. The upper position of the linear drive 16 constitutes the "start"- and the "reset-position" for a subsequent operation cycle. The start/reset-position, i.e. the upper position of the linear drive 16, is reached automatically upon switching on of the decapping system 10. As shown particularly in FIG. 5, the rotational drive for the screwing ring 56 is realized by means of a worm/gear arrangement 38, 48. Alternatively, a belt drive could be used. The linear movement of the linear drive 16 driven by drive 18 is realized by a threaded spindle. Alternatively, other driving concepts are conceivable as well. Upon modification of the decapping system 10, the lids 82 being unscrewed from the containers in a unscrewing cycle could be placed upon containers arranged within a cartridge system 28 having no lid-closure. Thus, the system according to the present invention is usable as well for screwing lids 82 or the like onto containers containing a reagent, and vice versa.

Figure 9:
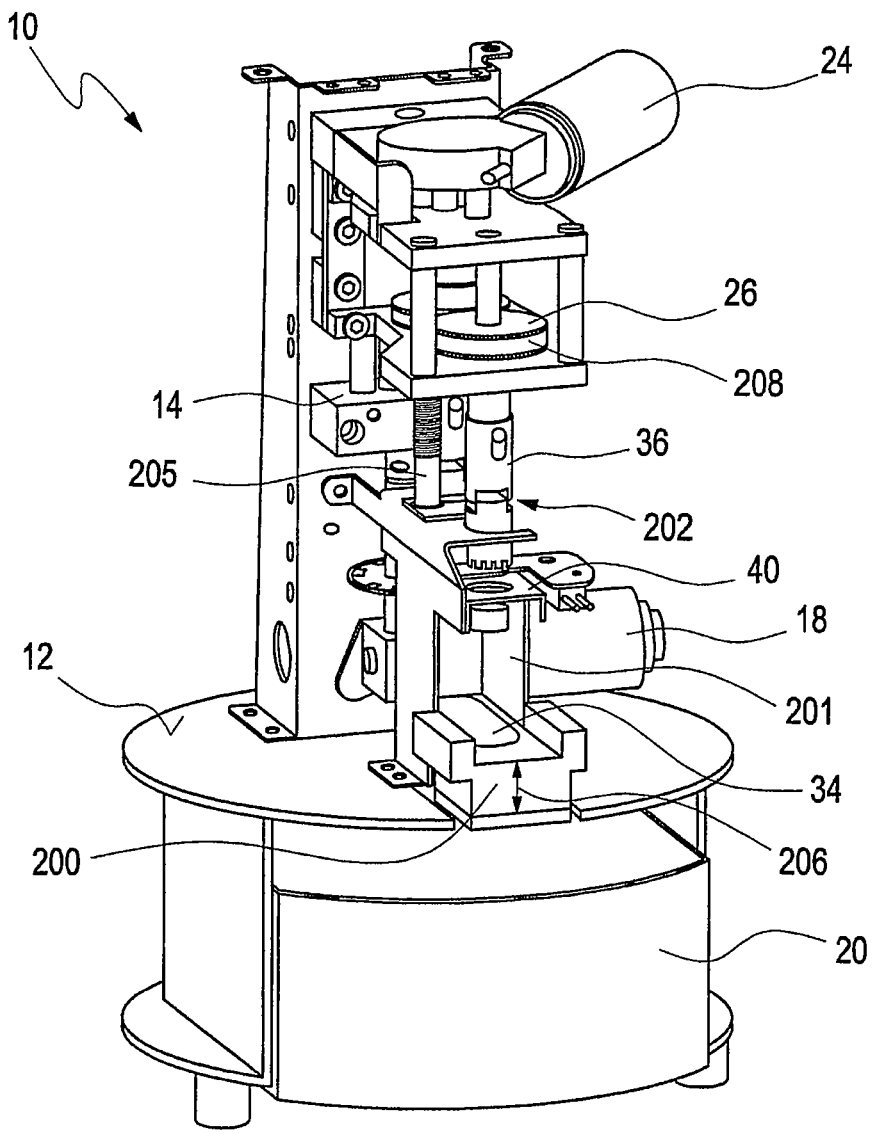
FIG. 9 is a perspective view of a second embodiment of the screwing/decapping system according to the present invention.

FIG. 9 shows a second embodiment of the decapping system according to the present invention. According to the second embodiment given in FIG. 9, the decapping system 10 comprises an adapting device 200. The adapting device is arranged below a guiding passage 201 of the decapping system 10. In the inactive position labeled with reference numeral 202 of the decapping system 10 according to the present invention, the adapting device 200 is used to compensate for different heights 30 of different cartridge systems 28 to be processed. By use of the adapting device 200, the processing height of various cartridge systems 28 with different heights 30 are increased.

The additional height/size compensation is labeled in FIG. 9 with reference numeral 206. Depending on the various cartridge systems 28 to be processed with the decapping system 10 according to the present invention, a corresponding number of adapting devices 200 each being configured for different height/size compensations 206 is used. The decapping system 10 according to FIG. 9 comprises the linear guide 14 for vertical movement of at least one screwing head 36—as shown in the second embodiment according to FIG. 9. The screwing head drive 24 comprises a belt drive 208 by means of which a rotational movement is transmitted onto the crown-shaped screwing ring 56 of the screwing head 36. By means of a positioning element 205, extending into a positioning opening 204 of the cartridge system 28, thereby together forming a positioning arrangement, the presence of a cartridge system 28 to be processed is detected (see FIG. 10). Below the crown-shaped screwing ring 56 of the screwing head 36 according to the present invention, the stripping device 40, being shaped as a fork-like element, is arranged. The position within a guiding passage 201, the cartridge system 28 arranged upon an adapting device 200, is maintained upon processing thereof. Reference numeral 18 depicts a drive which imposes the vertical movement onto the linear guide 14 onto which at least one screwing head 36 is arranged. The crown-shaped screwing ring 56 comprises the tooth-shaped protrusions 58 as given in greater detail in FIGS. 2 and 3, respectively, in the first embodiment of the present invention. The surface 12 of the decapping system 10 is provided with an opening 34, through which the lids 82 unscrewed from containers of the respective cartridge system 28 to be processed, are trashed into the lid-container 20 arranged underneath the surface 12 of the decapping system 10.

Figure 10:
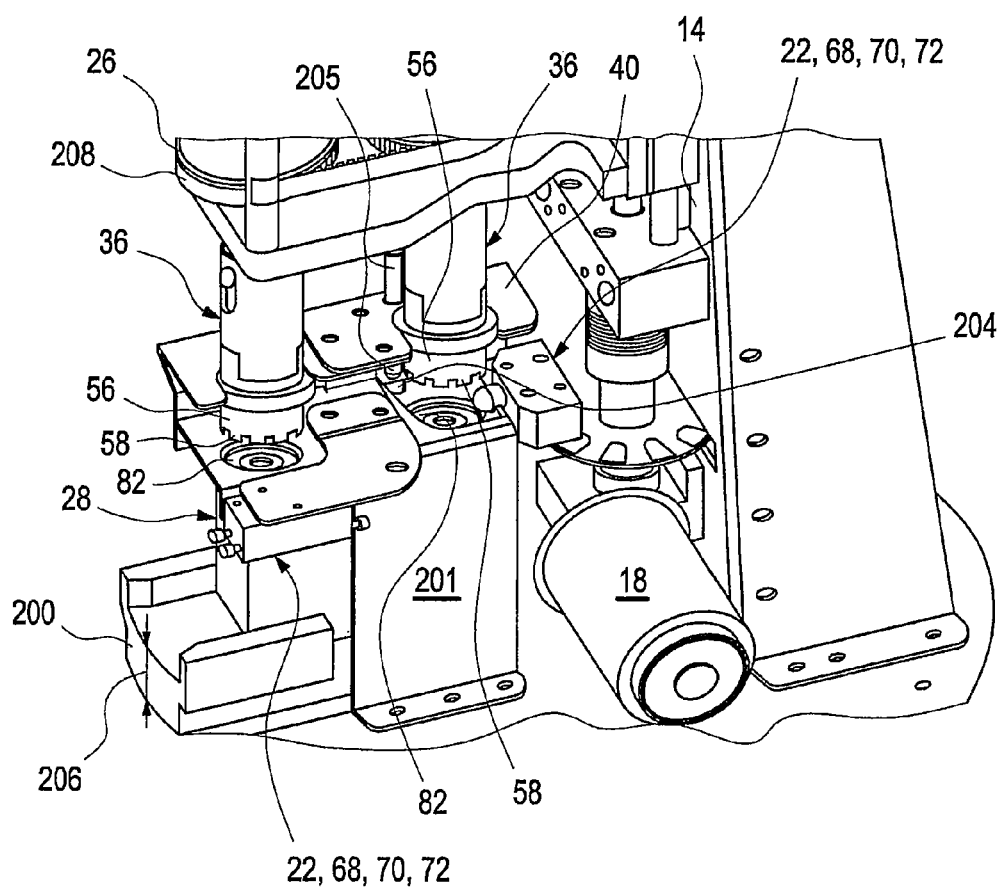
FIG. 10 is a partial perspective view of a cartridge system mounting area of the second embodiment according to FIG. 9.

FIG. 10 shows a cartridge system mounting area of the second embodiment given in FIG. 9. According to the detailed perspective view in FIG. 10, the cartridge system 28 is introduced into a guiding passage 201. The cartridge system 28 is arranged upon the adapting device 200 having a height compensation indicated by reference numeral 206. By means of the adapting device 200, the upper cartridge surface 32 is moved into the direction of the crown-shaped screwing ring 56 having a number of tooth-shaped protrusions 58 arranged along its outer circumference. The cartridge system 28 within the guiding passage 201 is fixed by an actuatable pin-shaped positioning element 205 engaging a positioning opening 204 on the upper cartridge surface 32 of the cartridge system 28 to be processed. The full introduction of the cartridge system 28 into the guiding passage 201 underneath the screwing head 36 is detected by means of micro-switches 22, 68, 70 and 72, which further initiate and stop the rotational movement of the crown-shaped screwing rings 56 and the vertical movement of the screwing heads 36 along the linear guide 14.

In FIG. 10, the positioning element 205 does not yet have engaged the positioning opening 205 on the upper surface 32 of the cartridge system 28. In FIG. 10, it is shown that the removing device 66 fits to an opening of the stripping device 40, shaped as a stripping fork. The rotational movement is transmitted to the crown-shaped screwing ring 56 of the two screwing heads 36 shown in FIG. 10 by means of the belt drive 208, in this embodiment being an alternative to the screwing head gear 26 of the first embodiment. The vertical movement of the screwing heads 36 is imposed thereupon by the drive 18 driving the linear guide 14 in vertical downward or upward direction, initiated by the micro-switches 22, 68, 70 and 72, respectively.

Figure 11:
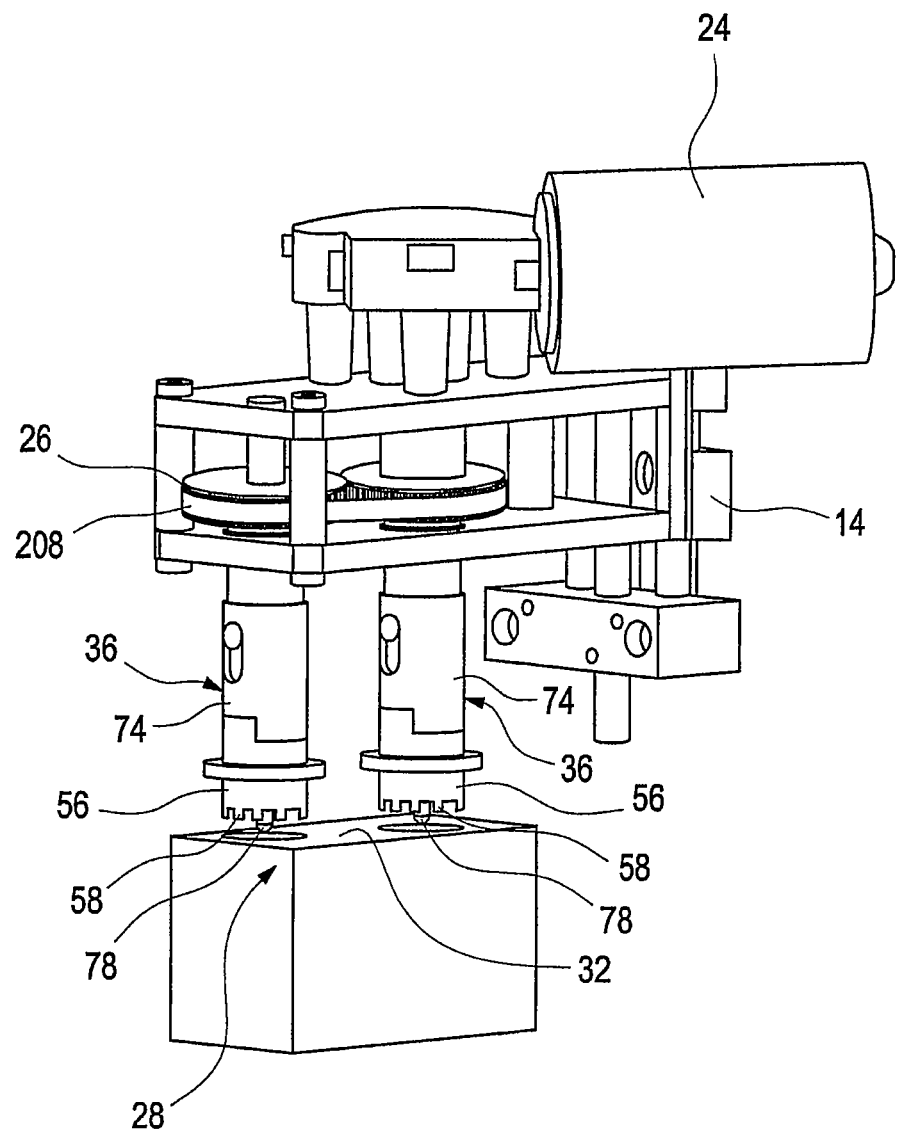
FIG. 11 is a perspective view of the screwing device of the second embodiment according to FIG. 9.

FIG. 11 shows the screwing head drive of the second embodiment according to FIG. 9 in more detail. The screwing drive for transmitting a rotational movement to the crown-shaped screwing ring 56 of the screwing head 36 comprises the screwing head drive 24 which is provided with a belt drive 208. The belt drive 208 constitutes an alternative to the worm/gear driving arrangement 38, 48 of the first embodiment shown in the present invention, see FIG. 5. From FIG. 11, it can be derived that both screwing heads 36 shown in this figure comprise the longitudinally slitted tensioning tool 60 for engagement of the funnel-shaped cavity 84 of the lid 82, as described in more detail in FIGS. 8A and 8B, respectively.

The crown-shaped screwing ring 56 of the screwing head 36 shown in FIG. 11 surrounds the tensioning tool 60 provided with a centering pin 62 and the previously mentioned centering cone 78 for engagement of the inner protrusion 94 of the funnel-shaped cavity 84 of the lids 82. The upper surface of the cartridge system 28 is labeled with reference numeral 32. Reference numeral 58 depicts tooth-shaped protrusions at the lower rim of the screwing head 36 which is spring biased as shown in greater detail in FIGS. 12A to 12D.

FIG. 12A to 12D each show details of the screwing head for use with the first and second embodiment of the present invention. The screwing head shown in FIG. 12A to 12D, respectively, may be used with both embodiments of the present invention, i.e. the decapping system 10 according to FIGS. 1A to 7, and the second embodiment of the present invention described hereinafter, i.e. the second embodiment according to FIGS. 9 to 11, respectively. The screwing heads 36 given in greater detail in FIGS. 12A to 12D provide for a more economic embodiment, since the first tensioning spring 50 as shown in FIG. 3 has been omitted. The tensioning tool 60 according to the embodiment given in FIGS. 12A to 12D is not spring biased. The distance from the toothed rim or tooth-shaped protrusions 58 of the crown-shaped screwing ring 56 to the holding-protrusion 76 according to the embodiments given in FIGS. 6 and 6A, respectively, is fixed. The first tensioning spring 50, which in the embodiment according to FIG. 3 is assigned to the tensioning tool 60, is omitted here.

Figures 12A, 12B:
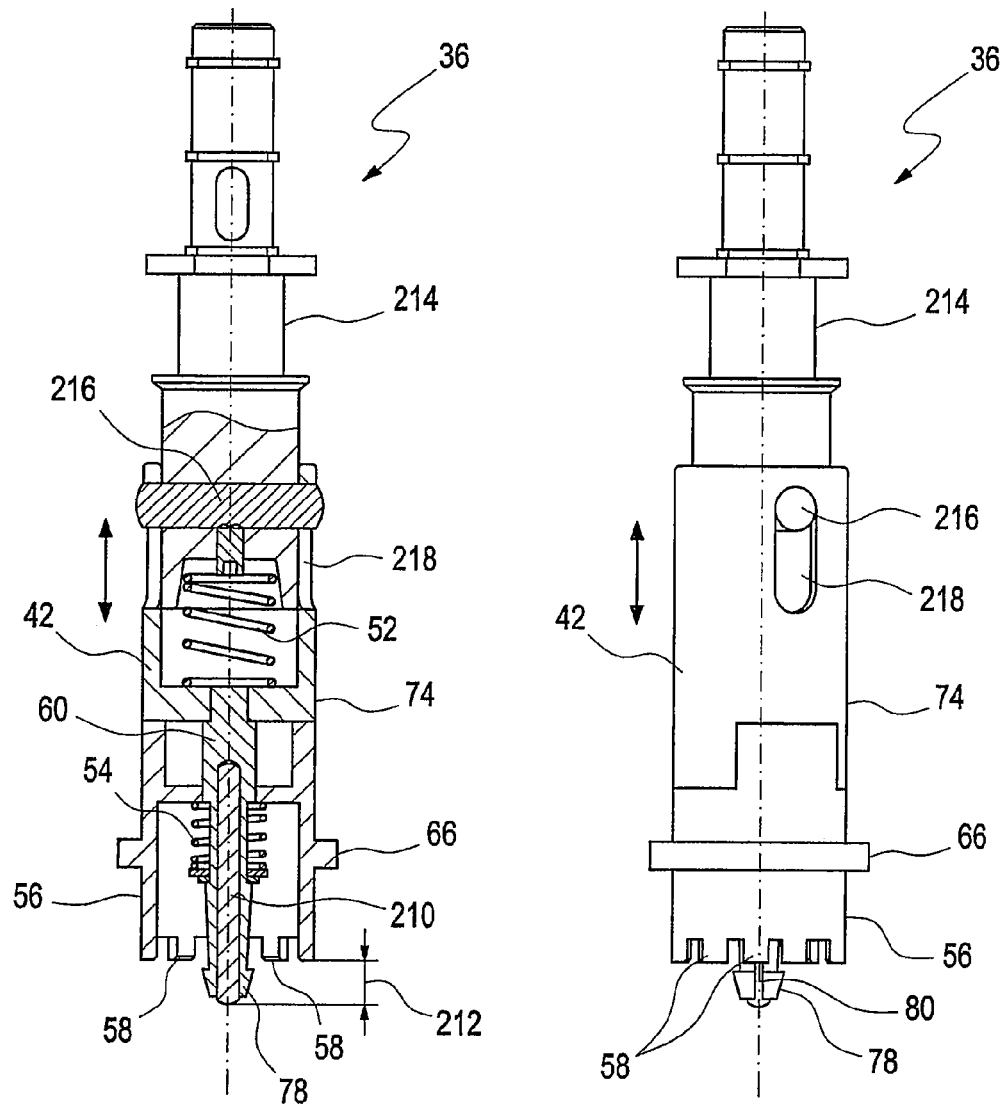
FIGS. 12A, 12B, 12C and 12D are section and side views showing details of screwing heads for use with the embodiments according to the present invention.

FIG. 12A shows the screwing head 36 comprising a piston 214. The piston 214 and the screw-support 42, having a hollow interior, are being engaged by one another by means of a bolt 216. The bolt 216 moves within a longitudinally slitted aperture 218 provided in the outer circumference of the screw-support 42. Within the screw-support 42, the second tensioning spring 52 is arranged. The second tensioning spring 52 pretensions the screw-support 42 in longitudinal direction, i.e. in Z-direction. Thus, the crown-shaped screwing ring 56 is spring biased and allows for compensation of axial movement. Surrounded by the crown-shaped screwing ring 56 is the tensioning tool 60 in this embodiment having a protection pin 210. The protection pin 210 protrudes below the tooth-shaped protrusions 58 on the downward rim about a protection distance 212. Thus, by means of the protection pin 210 being assigned to the tensioning tool 60, the damaging of the crown-shaped screwing ring 56 is prevented upon contact with an upper cartridge surface 32 of the cartridge system 28, since the protection pin 210 contacts the surface 32 prior to the crown-shaped screwing ring 56 contacting it. On the outer circumference of the crown-shaped screwing ring 56, the removing device 66 having a ring form, is provided.

According to FIG. 12A, the screwing head 36 is shown. From FIG. 12B, it becomes clear that the end portions of the bolt 216 are guided in the vertically oriented, longitudinally slitted aperture 218 on the outer circumference 74 of the screwing head 36. Screw-support 42 is spring-loaded by the second tensioning spring 52, the crown-shaped screwing ring 56 surrounds the centering cone 78 of the tensioning tool 60 provided with the protection pin 210.

Figures 12C, 12D:
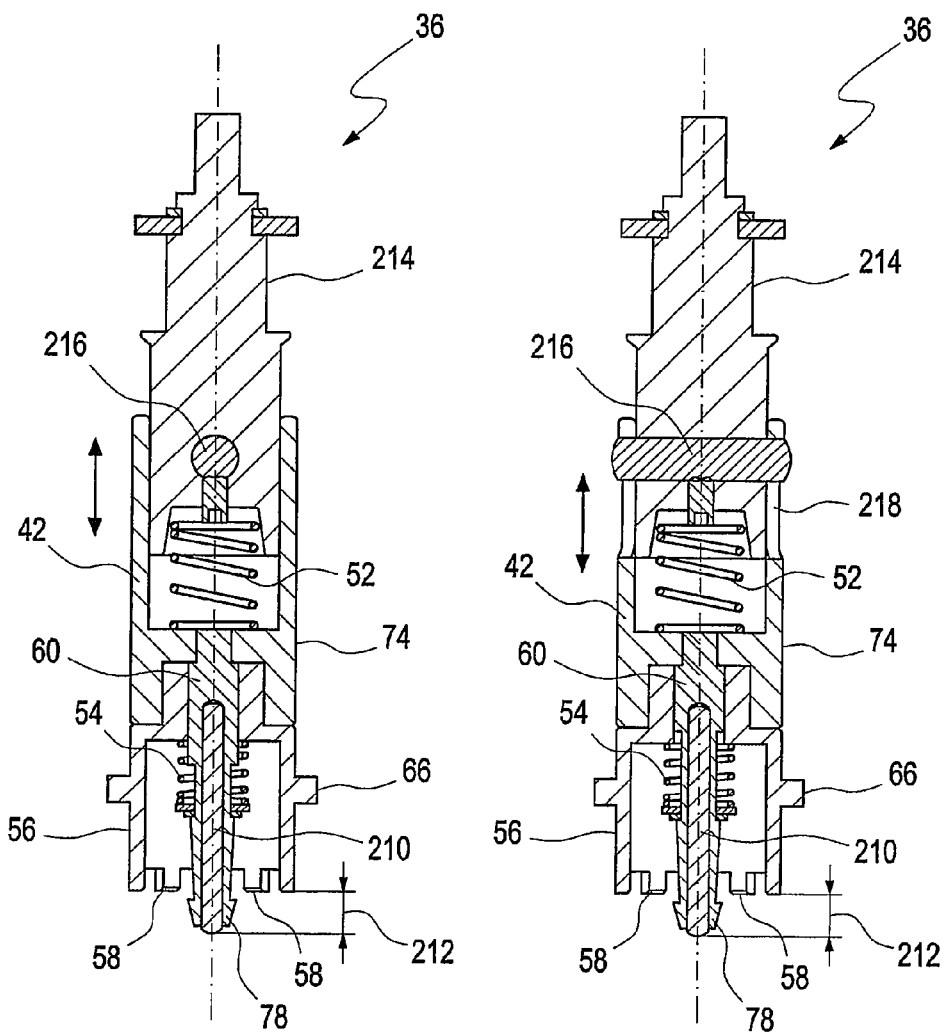

FIGS. 12C and 12D, respectively, show the screwing head in alternative embodiments. According to the embodiment of the screwing head 36 given in FIG. 12C, the screwing head 36 comprises the piston 214 and the bolt 216 by means of which the outer circumference 74 of the screw support 42 and the cylinder portion of the piston 214 thereof are coupled to each other. The third tensioning spring 54 is provided to reset the screwing head 36 into its initial position upon throwing off of the lid 82 by a relative movement between the crown-shaped screwing ring 56 relative to the tensioning tool 60. In the embodiment according to FIGS. 1A to 7, the lids 82 unscrewed are removed from the screwing heads 36 by means of a relative movement between a remover ring or removing device 66 relative to the centering pin 62. In the embodiment given in FIGS. 1A to 7, the decapping system 10 according to the present invention, the lids 82 being unscrewed, is pushed out of engagement of grooves 86 of the lid and the tooth-shaped protrusions 58 of the crown-shaped screwing ring.

Below the screw-support 42, the longitudinally extending tensioning tool 60 is shown. Within the tensioning tool 60 having a centering cone 78, the protection pin 210 is arranged. The protection pin 210 protrudes about the protection distance 212 below the tooth-shaped protrusions 58 of the crown-shaped screwing ring 56. Consequently, by means of the protection distance 212 upon contact with the cartridge system 28 protects the crown-shaped screwing ring 56 against damages when rotated. Due to the protection distance 212, the protection pin 210 contacts the cartridge system 28 arranged below the screwing head 36 prior to the tooth-shaped protrusions 58 at the lower ring of the crown-shaped screwing ring 56. The tensioning tool 60 is spring-loaded by the second tensioning spring 52.

On the outer circumference of the crown-shaped screwing ring 56, the removing device 66 is arranged. In the arrangement given in FIG. 12C, the protection pin 210 is pressed into the tensioning tool 60 spring-loaded by the second tensioning spring 52. According to the embodiments given in FIGS. 12C and 12D, the removing device 66 is integrated into the crown-shaped screwing ring 56, thus saving fastening means.

FIG. 12D shows the screwing head 36 according to FIG. 12C turned about 90°. From the perspective given in FIG. 12D, it becomes clear that the end portions of the bolt 216 are guided in the apertures 218 provided in the outer circumference 74 of the screw support 42 of the screwing head 36. The ends of the bolt 216 move within the longitudinally slotted apertures 218 arranged in the outer circumference 74 of the screw support 42. The crown-shaped screwing ring 56 is biased by the second tensioning spring 52. Likewise, the tensioning tool 60 is biased by the third tensioning spring 54, the protection pin 210 arranged in a protection distance 212 with respect to the lowering of the toothed, crown-shaped screwing ring 56.

The second embodiment according to the decapping system 10 given in greater detail in FIGS. 9 to 11 shows a positioning element 205 for engagement of a positioning opening 204 of the cartridge system 28 to be processed. Thus, the cartridge system 28 is fixed before the operation cycle is started, providing a safety feature for the operating person.

According to the second embodiment of the present invention given in more detail in FIGS. 9 to 11, a height compensation 206 is performed by the adapting device 200. The screwing operation is, upon downward movement of the screwing head 36, started always at the same position upon detection of the presence of a cartridge system 28 to be processed by micro-switches on the guiding passage 201 or at lateral positions.

A cartridge system 28 having a too large, excessive height 30 cannot be processed by the decapping system 10 according to FIGS. 9 to 11, since it would not fit into the guiding passage 201 of the decapping system 10 according to FIGS. 9 to 11. Is the cartridge system 28, however, too low, the operating cycle is not being initiated, since the cartridge system 28 being too low does not contact within the guiding passage 201 a micro-switch.

Alternatively, it is conceivable that the lids 82 are not trashed into the lid container 20 arranged underneath the surface 12 of the decapping system 10 according to the present invention, but instead in a subsequent cycle new lids are screwed upon a cartridge system 28 or screwed upon containers with a cartridge system 28. Instead of a movement of the screwing head 36 in direction to the cartridge system 28 to be processed, vice versa the cartridge system 28 may be moved towards the screwing heads 36 of the decapping system 10 according to the present invention, which in this alternative, however, are mounted stationary. The transport and the removal of the cartridge systems 28 to be processed is automatically performed by linear drives, as shown in the accompanying drawings, to realize for a fully automatic processing of a number of cartridge systems 28.

The decapping system 10 according to the embodiments of the present invention shows the rotational movements and the sliding movements of the crown-shaped screwing rings 56 and the screwing heads 36 being detected by means of micro-switches 22, 68, 70 and 72, respectively. Instead of the micro-switches 22, 68, 70, 72, sensors, such as hall sensors, or optical devices such as light barriers or the like could be used as an alternative. The decapping system 10 according to both embodiments being described above is to be implemented using one screwing head 36 only, as well this would require less space for the decapping system 10 for installation thereof.

In view of the above it is to be appreciated that the present invention in one embodiment provides for a flexible opening of containers, being filled with a reagent which allows for a parallel processing of containers and cartridge systems, independent of the number of containers of the cartridge system at a time, independent of the height and size of the containers containing the reagents, and still further independent on the size and height of the cartridge system.

According to another embodiment of the present invention, a decapping device is provided which, due to the shape and the arrangement of the screwing heads, allows for a parallel processing of a number of containers being stored in a cartridge system. Particularly, the cartridge system contains two or more reagents containing containers at randomized positions within the cartridge system. The decapping device according to the present invention allows for processing of an entire cartridge system having a selected number of containers in a synchronous manner within one cycle. The at least one screwing head of the decapping system according to an embodiment of the present invention allows for processing of a cartridge system having a randomized number of containers in a synchronous way in a single working cycle and particularly to unscrew all threaded lids to trash the threaded lids which are no longer used for various reasons.

Although not limited thereto, a major advantage of the embodiments of the present invention is the fact that the decapping system allows for a parallel processing of a cartridge system which either can only have one single container or, in the alternative, may have a number of containers to be processed in a parallel way. Still further, it is of no significance at which positions the containers with the reagents are arranged within the cartridge system. The at least one screwing head or a plurality of screwing heads according to an embodiment of the present invention automatically detect variable sizes, particularly variable heights of the cartridge system and, upon detection thereof, process the cartridge system, independent of the height thereof and independent of the order of the reagent containers within the cartridge system.

In an alternative embodiment, a processing of a cartridge system having different sizes and particularly different heights by means of suitable adapters is realized. The alternative system identifies a cartridge system being too small, i.e. having a low height, and does not further process the cartridge unit previously identified. Still further, the adapting device is handled in an ergonomic way, i.e. the adapting device can be fixed by means of a magnetic force. This allows in case of malfunction, for instance, the threaded lid somewhere being blocked within the system, to move the adapting device first and remove the cassette being processed and/or the threaded lid. By means of a different number of adapting devices, cartridge systems of different heights are processed very easily upon exchange of the adapting device, only. The cartridge system is fixed by a holding arrangement and the user of the system according to an embodiment of the present invention is hindered to interrupt the processing of the cartridge system presently being processed.

Still further, the at least one screwing head in embodiments of the present invention is biased by at least one spring element which allows a tensioning force being exerted on the at least one screwing head and which allows for a grip of cartridge systems having threaded lids of different heights. Still further, the at least one spring biased screwing head exert upon processing of the threaded lids a force on the lids to allow for a firm contact between the at least one screwing head and the lid to be processed. The lids unscrewed are being processed by means of an annular-shaped stripping element. A stripping device such as a stripping fork or the like, being shaped corresponding to the geometry of the annular stripping member, removes the lids unscrewed from the at least one screwing head. The lids unscrewed are being stripped by the holding element of the entering pin and are trashed into a container being arranged underneath the cartridge system. This avoids a further movement of the screwing head to a trashing position and reduces complexity thereof.

The screwing head according to an embodiment of the present invention comprises a spring biased crown-shaped element similar to a socket wrench which engages an outer toothing of the threaded lid and removes same by rotational movement thereof. The screwing head comprises for centering purposes relative to the threaded lid a centering pin being centrally arranged and which centers the screwing head in a funnel-shaped cavity of the threaded lid and which engages a portion of the threaded lid by a snapping movement. Thus, the threaded lid is fixed to the at least one screwing head. The biasing element, such as a universal ball joint or the like, of the centering pin acts as a tensioning tool in radial outward extending direction and compensates for manufacturing tolerances of the threaded lid.

Still further, the decapping devices according to an embodiment of the present invention comprises a suitable number of screwing heads such as, for example, two or three screwing heads. The screwing heads are supported by spring elements which allow for the processing of different sizes and heights of threaded lids and cartridge systems. A non-presence of threaded lids is compensated for by a rearward movement of the entire spring-mounted screwing head. With the screwing head being pretensioned, it is not necessary to move the screwing head upon a screwing process synchronously to the pitch of the threading in vertical direction, the screwing process is performed in a stationary position due to the spring biased embodiment of the screwing head. The centering pin comprises a resilient lid holding device. In an advantageous embodiment, the lid holding device is made as a slitted, biased tensioning tool, such as a chuck, or is arranged as an O-ring-spring device. The entire centering pin including a protection pin is arranged separately within the screwing heads and is subjected to springs allowing for compensation of manufacturing tolerances of the threaded lids. Still further, a secure engagement of the tensioning tool within a recess of the threaded lid is assured.

Within the centering pin, the protection pin is provided which protrudes from the tensioning tool, such as a chuck. The protection pin protects the tensioning tool of the centering pin against deformation or damage in general, which may occur upon erroneous or intended touching of the centering pin and the tensioning tool or chuck onto a solid surface, such as the upper surface of the cartridge system upon non-presence of a threaded lid in the respective position.

The fixing of the cartridge system in a certain position is realized by a fixing pin which engages an opening of the cartridge system and therefore realizes a connection to the cartridge system upon processing thereof. After unscrewing, the lids from the containers of the cartridge system, the cartridge system is being released by the fixing pin. Alternatively, the fixing pin may be shaped as a sliding element contacting the cartridge system on the outer surface thereof.

The annular-shaped stripping member for trashing the threaded lids unscrewed from the container is actuatable from the outside of the screwing head and moves, due to its resiliency, after trashing of the lids automatically back into the starting position. The removal of the lid previously unscrewed is performed by a vertical movement of the at least one screwing head upon contact between the annular-shaped stripping member and the stationary arranged stripping device, such as shaped as a stripping fork. A movement of the stripping device into the opposite vertical direction is conceivable, the annular-shaped stripping element being stationary mounted. The trashing of the lids being unscrewed in the container arranged below the screwing head is activated after the cartridge system has been removed from the desk top below the screwing head.

For processing of a semi-automatic screwing system according to the present invention, additional embodiments are conceivable. For example, in one embodiment, a control is realized by the use of micro-switches. The entire cycle and the detection of the presence or non-presence of a cartridge system, particular the height and the size thereof, is managed only by micro-switches. Secondly, in another embodiment, a control via software implementation is conceivable. Rotational speeds, moving paths, velocities etc. are configured within a software system such as, for example, a controller 220 (FIG. 1B).

In another embodiment, an optical device 222 (FIG. 1B) provides for detection of the level of the lid container 20. In one embodiment, the optical device 222 uses a conventional LED technique which saves the use of an additional display in the front portion of the system and facilitates the detection of the fill level of the container 20 (i.e., trash-bin) arranged below the screwing heads 36. In another embodiment, a front portion of the lid container 20 is made of a transparent material, to allow for a quick and easy detection of the fill level of the lid container. Further, in another embodiment, the optical device 222 indicates the readiness of the device 10 for operation, also saving an additional display in the front portion of the system.

In compliance with the statute, the invention has been described in language more or less specific as to structural and methodical features. It is to be understood, however, that the invention is not limited to the specific features shown and described, since the means herein disclosed comprise preferred forms of putting the invention into effect. The invention is therefore, claimed in any of its forms or modifications within the proper scope of the appended claims appropriately interpreted in accordance with the doctrine of equivalents. Any modification of the present invention that comes within the spirit and scope of the following claims should be considered part of the present invention.

What is claimed is:

1. A decapping system for opening reagent containers stored in a cartridge system closed by lids, said lids being removed and secured by a rotational movement,
    said decapping system having a centering unit, said centering unit having at its lower end an element for engaging a lid,
    said decapping system has at least one driven and vertically movable screwing head,
    said screwing head comprises an axial screw support on a crown-shaped screwing ring being spring-loaded by at least one tensioning spring allowing for a relative movement between said crown-shaped screwing ring and said screw support, such that a vertical movement of said lid engaged by said crown-shaped screwing ring with respect to said container during rotational movement of said lid relative to said container is compensable.

2. The decapping system according to claim 1, wherein said at least one screwing head is arranged on a linear drive movable in a vertical direction.

3. The decapping system according to claim 1, wherein said at least one driven and vertically movable screwing head is two screwing heads.

4. The decapping system according to claim 1, wherein said crown-shaped screwing ring comprises a plurality of tooth-shaped protrusions arranged along the circumference of a rim of said crown-shaped screwing ring.

5. The decapping system according to claim 1, wherein said crown-shaped screwing ring is provided with a removing device.

6. The decapping system according to claim 1, wherein said centering unit comprises a tensioning tool having a centering cone engaging a lid to be processed.

7. The decapping system according to claim 6, wherein said tensioning tool is preloaded by a tensioning spring within said screwing head.

8. The decapping system according to claim 6, wherein said centering cone comprises an annularly extending ring-shaped holding protrusion.

9. The decapping system according to claim 6, wherein an end portion of said tensioning tool comprises a plurality of longitudinally extending slits for creation of a tensioning force in a radial direction.

10. The decapping system according to claim 6, wherein said tensioning tool comprises a protection pin.

11. The decapping system according to claim 10, wherein said protection pin protrudes about a protection distance with respect to a plurality of tooth-shaped protrusions of said crown-shaped screwing ring.

12. The decapping system according to claim 6, wherein said tensioning tool includes a centering pin biased by a first tensioning spring with respect to said screw support of said screwing head and/or is spring-loaded by a third tensioning spring with respect to said screwing ring.

13. The decapping system according to claim 1, wherein said cartridge system to be processed is fixed by a positioning arrangement.

14. The decapping system according to claim 1, wherein the relative position of a surface of said cartridge system to be processed relative to said crown-shaped screwing ring of said at least one screwing head is adjusted by means of an adapting device.

15. The decapping system according to claim 14, wherein said adapting device compensates for a variable height of said cartridge system.

16. The decapping system according to claim 1, wherein said decapping system comprises a surface onto which a linear guide for a linear drive is arranged, an opening is provided and underneath of which a lid container for containing lids unscrewed by said screwing head from a number of reagent containers is arranged.

17. The decapping system according to claim 1, wherein said screwing head comprises a stripping device which after removal of a previously engaged lid turns back into its inactive position automatically.

18. The decapping system according to claim 17, wherein said stripping device is shaped as a stripping fork.

19. A decapping system for opening reagent containers stored in a cartridge system closed by lids, said lids being removed and secured by a rotational movement, said decapping system having a centering unit, said centering unit having at its lower end an element for engaging a lid, said decapping system has at least one driven and vertically movable screwing head, said screwing head comprises an axial screw support on a crown-shaped screwing ring being spring-loaded by at least one tensioning spring allowing for a relative movement between said crown-shaped screwing ring and said screw support, such that a vertical movement of said lid engaged by said crown-shaped screwing ring with respect to said container during rotational movement of said lid relative to said container is compensable, said screwing head cooperating with a stripping device for removal of said lid being unscrewed and previously being engaged.

* * * * *

UNITED STATES PATENT AND TRADEMARK OFFICE
CERTIFICATE OF CORRECTION

PATENT NO. : 8,474,225 B2  
APPLICATION NO. : 13/471786  
DATED : July 2, 2013  
INVENTOR(S) : Reinhold Krämer et al.

Page 1 of 1

It is certified that error appears in the above-identified patent and that said Letters Patent is hereby corrected as shown below:

Title Page, item (12) and (75) Inventor: "Reinhold Kramer, Peissenberg (DE)" should read --Reinhold Krämer, Peissenberg (DE)--

Signed and Sealed this  
Twenty-fourth Day of June, 2014

Michelle K. Lee  
*Deputy Director of the United States Patent and Trademark Office*